United States Patent [19]

Honma et al.

[11] 4,332,809
[45] Jun. 1, 1982

[54] PYRIDINECARBOXAMIDE DERIVATIVES AND PROCESS FOR THE PREPARATION THEREOF

[75] Inventors: Yasushi Honma, Ageo; Mikio Takeda, Urawa; Kei Tsuzurahara, Ageo, all of Japan

[73] Assignee: Tanabe Seiyaku Co., Ltd., Osaka, Japan

[21] Appl. No.: 231,787

[22] Filed: Feb. 5, 1981

[30] Foreign Application Priority Data

Feb. 15, 1980 [JP] Japan ................................. 55-18008

[51] Int. Cl.³ .................. A61K 31/455; C07D 401/12
[52] U.S. Cl. .................................... 424/266; 546/276; 549/420
[58] Field of Search .......................... 546/276; 424/266

[56] References Cited
U.S. PATENT DOCUMENTS 3,824,249  7/1974  Regnier et al. ..................... 546/276
4,129,735  12/1978  Sellstedt et al. ..................... 546/276

Primary Examiner—Ethel G. Love

Attorney, Agent, or Firm—Linda G. Bierman; Jordan B. Bierman

[57] ABSTRACT

N-(5-Tetrazolyl)-6-phenyl-2-pyridinecarboxamide derivatives of the formula:

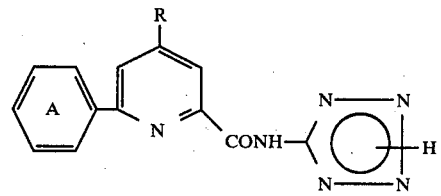

wherein R is hydrogen, a halogen, a lower alkyl or a lower alkoxy, and the phenyl ring A is a phenyl having a substituent selected from the group consisting of amino, a mono(lower)alkylamino, a di(lower)alkylamino, or a lower aliphatic acylamino, and a pharmaceutically acceptable salt thereof, and process for the preparation thereof. Said pyridinecarboxamide derivatives have excellent anti-allergic activities even by oral administration and are useful as an anti-allergic medicine.

7 Claims, No Drawings

PYRIDINECARBOXAMIDE DERIVATIVES AND PROCESS FOR THE PREPARATION THEREOF

The present invention relates to novel pyridinecarboxamide derivatives and a process for the preparation thereof. More particularly, it relates to N-(5-tetrazolyl)-6-phenyl-2-pyridinecarboxamide derivatives of the formula:

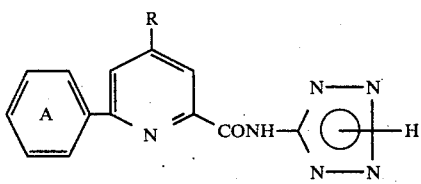

wherein R is hydrogen, a halogen, a lower alkoxy or a lower alkyl, and the phenyl ring A is substituted with a mono(lower)alkylamino, a di(lower)alkylamino, or a lower aliphatic acylamino, or a pharmaceutically acceptable salt thereof, and a process for the preparation thereof.

The compounds [I] of the present invention have two isomeric structures: 1H-isomer and 2H-isomer in the tetrazole ring as shown in the following formulae, which are mutually converted from one to another. These isomers are both included within the present invention.

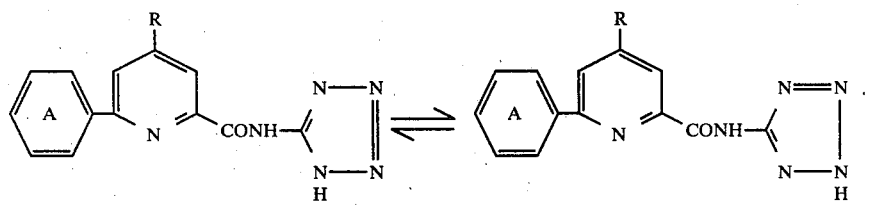

wherein R and the ring A are as defined above.

The compounds [I] of the present invention are novel compounds and have excellent anti-allergic activities and are useful as a medicine. Particularly, the compounds [I] are characteristic in that they can show excellent anti-allergic activities even by administering in oral route.

In the formula [I], the group "R" include hydrogen, a halogen, able compound is N-(5-tetrazolyl)-4-methyl-6-(4-methylaminophenyl)-2-pyridinecarboxamide.

The compounds [I] can be used as a medicine in the form of a free compound or a pharmaceutically acceptable salt thereof. Suitable examples of the pharmaceutically acceptable salt are an alkali metal salt (e.g. sodium salt, potassium salt, lithium salt), an organic amine salt (e.g. triethanolamine salt, tris(hydroxymethyl)aminomethane salt), a basic amino acid salt (e.g. lysine salt), an inorganic acid addition salt (e.g. hydrochloride, sulfate, phosphate), nitrate), an organic acid addition salt (e.g. acetate, lactate, tartrate, fumarate, maleate, oxalate, succinate, methanesulfonate, benzoate), or the like.

The compounds [I] or their salts can be administered in oral or parenteral route when used as a medicine. These compounds may be used in admixture with conventional pharmaceutically acceptable carrier or diluent. Suitable examples of the carrier or diluent are gum arabic, gelatine, sorbitol, tragacanth gum, polyvinylpyrrolidone, lactose, sucrose, potassium phosphate, magnesium stearate, talc, potato starch, or the like.

The compounds of the present invention and compositions thereof can be used in conventional types of preparations, for example, solid preparations such as tablets, pills, powders, capsules, granules, or liquid preparations such as emulsions, suspensions, solutions, or the like. When they are administered in parenteral route, they may be used in the form of an injection.

The therapeutic dose of the pyridinecarboxamide derivative [I] or its salt depends on route of administration; the conditions of diseases; and the particular diseases to be treated. In general, it may be used at a dose of about 0.2 to about 120 mg (in terms of free base), especially about 1 to about 60 mg (in terms of free base), per kilogram of body weight per day in the case of oral administration.

-continued

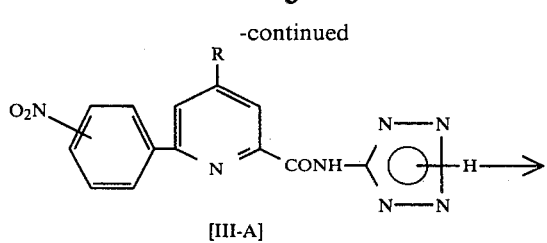

[III-A]

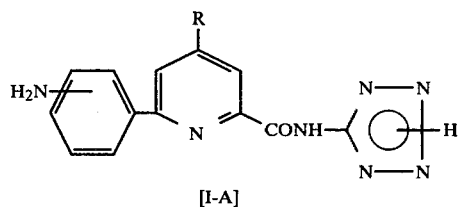

[I-A]

Reaction Scheme-II:

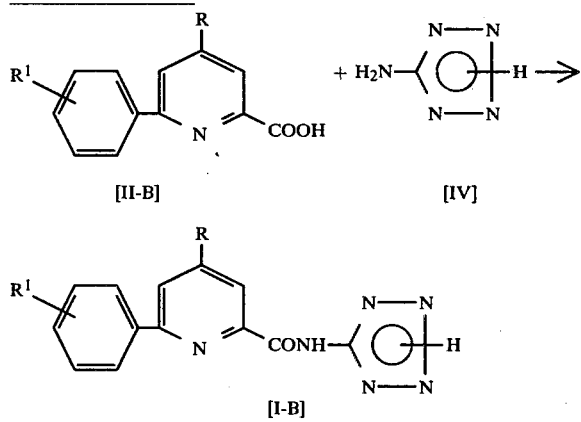

Reaction Scheme-III

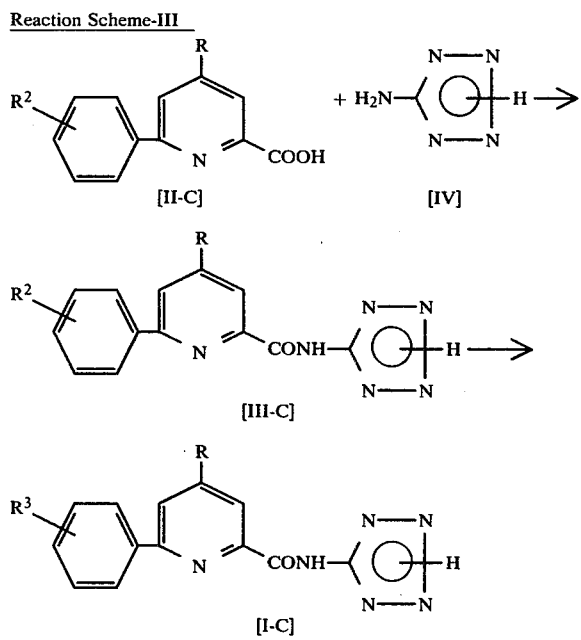

In the above formulae, R is as defined above, $R^1$ is a di(lower)alkylamino or a lower aliphatic acylamino which are the same as a part of the substituents on the phenyl ring A as defined above, $R^2$ is amino or a mono(-lower)alkylamino which are the same as a part of the substituents on the phenyl ring A as defined above, provided that said amino group is protected by an appropriate protecting group such as benzyloxycarbonyl, p-methoxybenzyloxycarbonyl, tert-butoxycarbonyl, tert-amyloxycarbonyl, etc., and $R^3$ is a group obtained after removing the amino-protecting group from the above groups for $R^2$.

That is, the compounds [I-A] can be prepared by subjecting 6-phenyl-2-pyridinecarboxylic acid derivative [II-A] and 5-aminotetrazole [IV] to condensation reaction, and reducing the resulting compound [III-A] in order to convert the nitro group into amino group. The compounds [I-B] can be prepared by subjecting 6-phenyl-2-pyridinecarboxylic acid derivative [II-B] and 5-aminotetrazole [IV] to condensation reaction. The compounds [I-C] can be prepared by subjecting 6-phenyl-2-pyridinecarboxylic acid derivative [II-C] and 5-aminotetrazole [IV] to condensation reaction, and removing the amino-protecting group of the resulting compound [III-C].

These reactions are explained in more detail below.

Condensation reaction:

The condensation reaction of the starting compounds [II-A], [II-B] and [II-C] with 5-aminotetrazole [IV] can be carried out by conventional methods which are usually used for forming an acid amide bond in peptide chemistry. For instance, when a free carboxylic acid compound is used as the starting material, the reaction can be carried out in an appropriate solvent in the presence of an appropriate condensing agent. Suitable examples of the condensing agent are N,N'-carbonyldiimidazole, N,N'-dicyclohexylcarbodiimide. Suitable examples of the solvent are tetrahydrofuran, dioxane, dimethylformamide. The reaction proceeds preferably at a temperature of $-10°$ to $100°$ C.

When a reactive derivative of carboxylic acid is used as the starting material, the reaction can be carried out by the conventional acid halide method, mixed acid anhydride method, etc., preferably acid halide method. The acid halide method can be carried out by reacting an acid halide of the compound [II-A], [II-B] or [II-C] with 5-aminotetrazole in an appropriate solvent in the presence of an appropriate acid acceptor. Suitable examples of the acid acceptor are organic bases (e.g. triethylamine, pyridine), alkali metal carbonates (e.g. sodium carbonate, sodium hydrogen carbonate). Suitable examples of the solvent are dimethylformamide, dioxane, etc. When an organic base is used in a large amount as the acid acceptor, it acts also as a solvent, and hence no further solvent is required. The reaction proceeds preferably at a temperature of $20°$ to $120°$ C.

The acid halide (e.g. acid chloride) of the compound [II-A], [II-B] or [II-C] can be obtained by treating the corresponding free carboxylic acid with a halogenating agent, such as thionyl chloride, phosphorus oxychloride, phosphorus pentachloride. The halogenating reaction is preferably carried out in an appropriate solvent at a temperature of from $0°$ C. to the reflux temperature of the halogenating agent. Suitable examples of the solvent are benzene, toluene, pyridine, etc., but when the halogenating agent is used in an excess amount, the halogenating agent acts also as the solvent and hence further solvent is not necessarily required.

When the condensation reaction is carried out by a mixed acid anhydride method, the starting compound [II-A], [II-B] or [II-C] is reacted with ethyl chloroformate, isobutyl chloroformate, or the like, and the resulting mixed acid anhydride of the compound [II-A], [II-B] or [II-C] is reacted with 5-aminotetrazole in an appropriate solvent (e.g. tetrahydrofuran, dioxane, di-

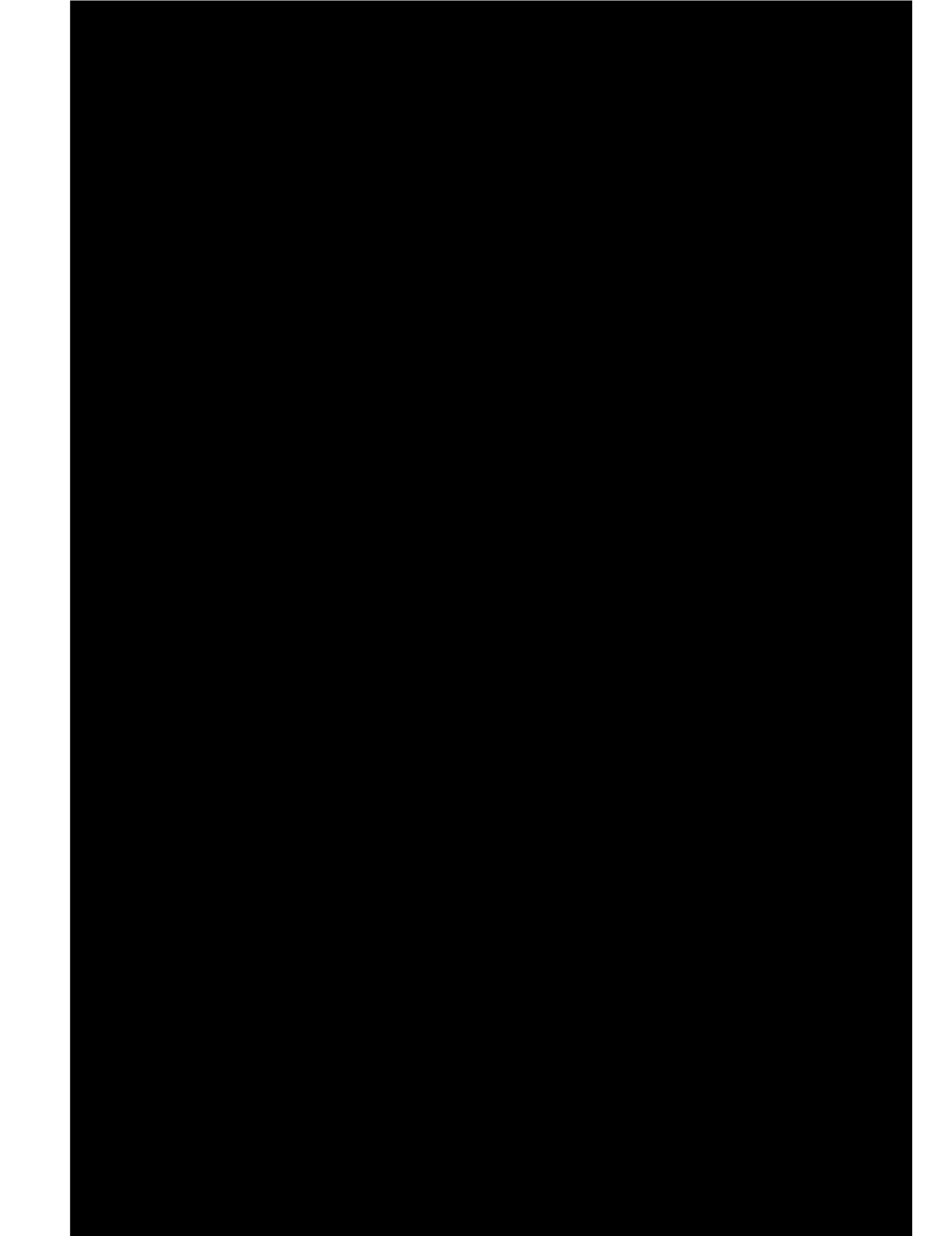

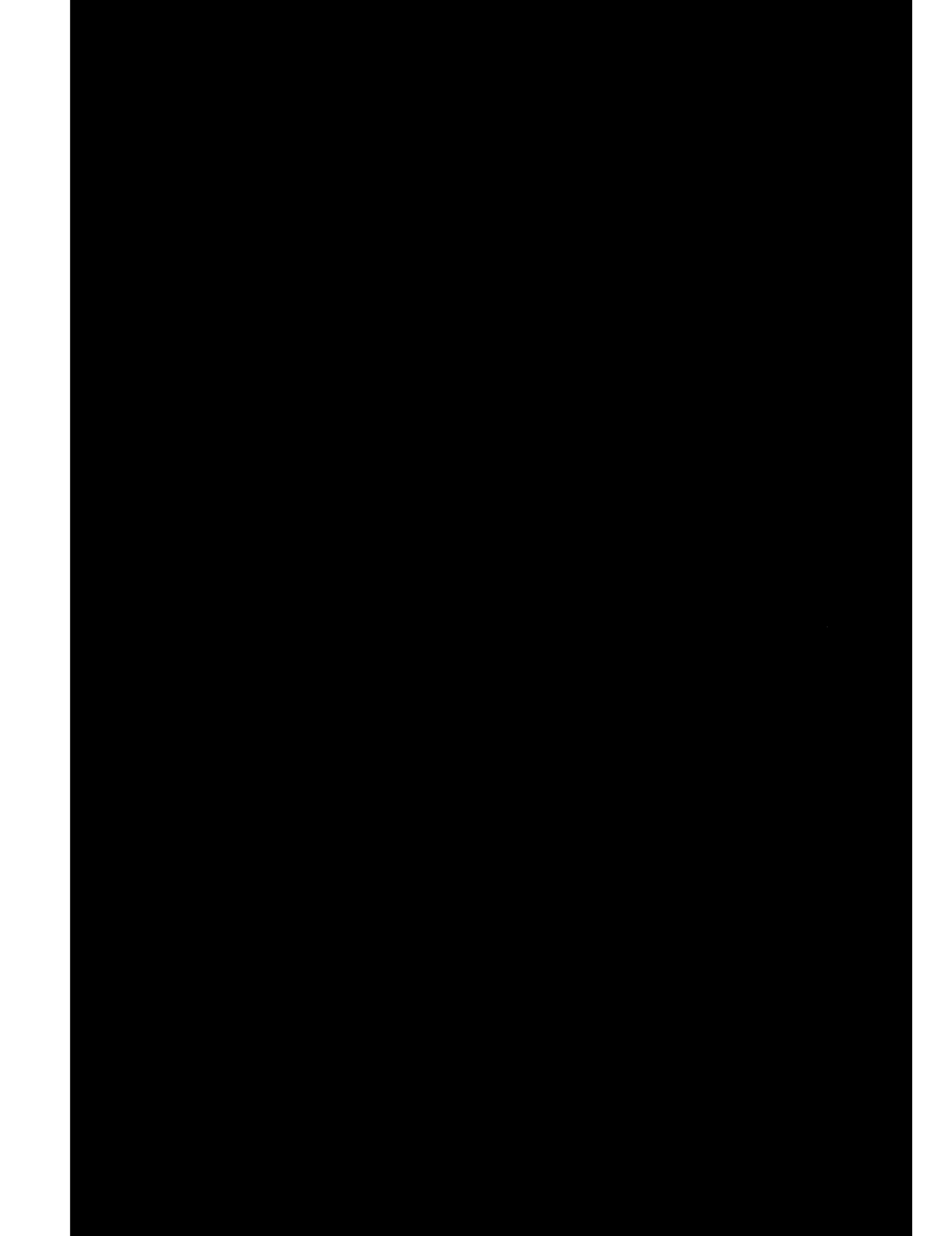

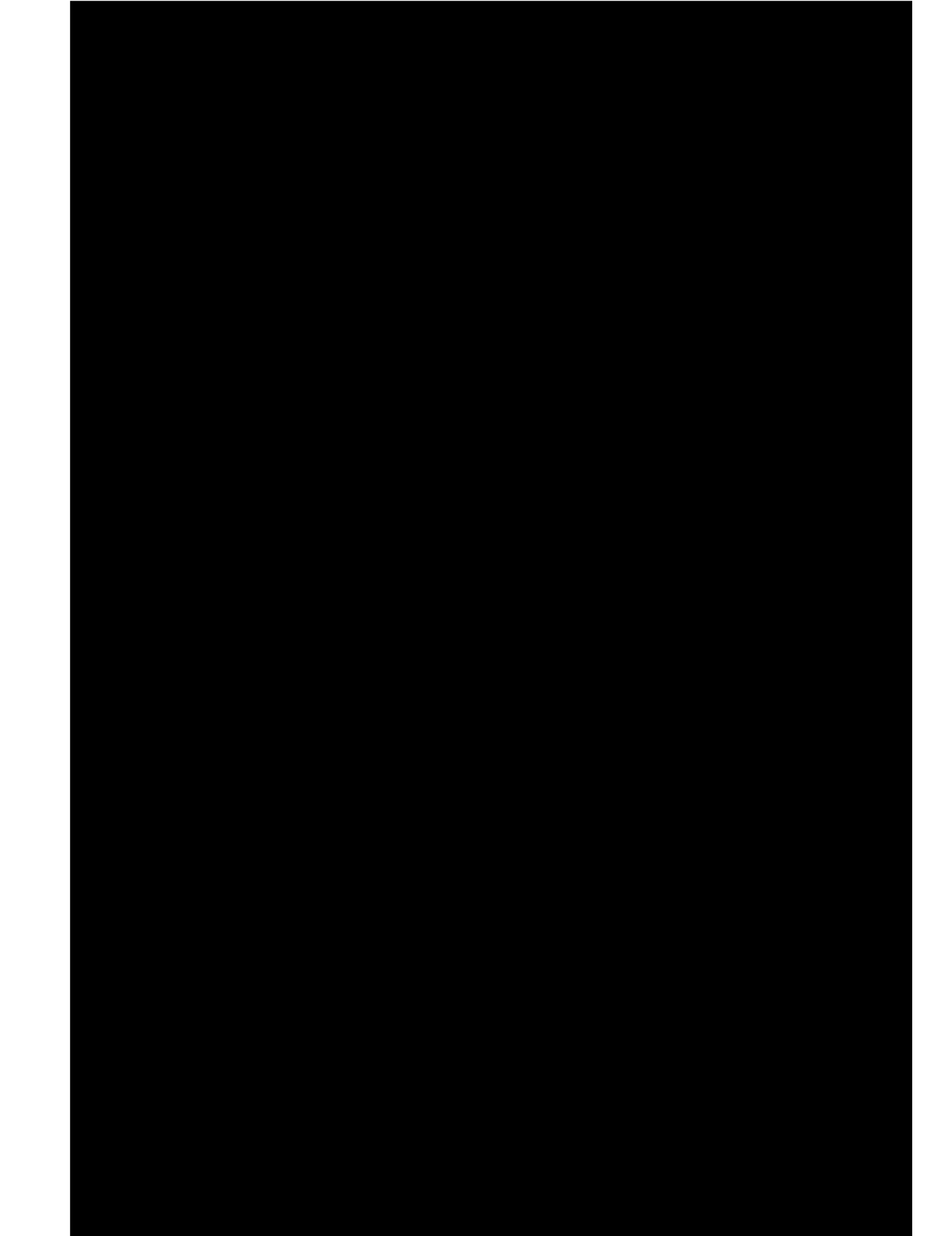

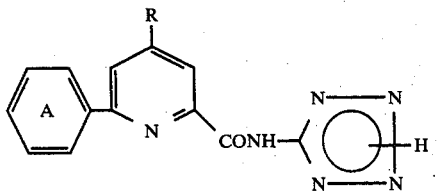

wherein R is hydrogen, straight chain alkyl having 1 to 4 carbon atoms, straight chain alkoxy having 1 to 3 carbon atoms, or chlorine, and A is aminophenyl, methylaminophenyl, ethylaminophenyl, dimethylaminophenyl, or diethylaminophenyl, or a pharmaceutically acceptable salt thereof.

2. The derivative of claim 1 wherein A is 4-aminophenyl, 4-methylaminophenyl, 4-ethylaminophenyl, 4-dimethylaminophenyl, or 4-diethylaminophenyl.

3. The derivative of claim 1 wherein, when R is hydrogen or straight chain alkyl having 1 to 4 carbon atoms, A is 4-aminophenyl or 4-methylaminophenyl; when R is straight chain alkoxy having 1 to 3 carbon atoms, A is 4-aminophenyl, 4-ethylaminophenyl, 4-dimethylaminophenyl, or 4-diethylaminophenyl; and when R is chlorine, A is 4-aminophenyl.

4. The compound of claim 1, which is N-(5-tetrazolyl)-4-methyl-6-(4-methylaminophenyl)-2-pyridinecarboxamide or a pharmaceutically acceptable salt thereof.

5. A composition for treatment of an anaphylaxis which comprises an amount of a compound of claim 1 such that, when administered to a warm blooded animal, it will provide an anti-anaphylactic amount of said compound.

6. A composition for treatment of an anaphylaxis which comprises an amount of a compound of claim 2 such that, when administered to a warm blooded animal, it will provide an anti-anaphylactic amount of said compound.

7. A composition for treatment of an anaphylaxis which comprises an amount of a compound of claim 3 such that, when administered to a warm blooded animal, it will provide an anti-anaphylactic amount of said compound.

* * * * *

UNITED STATES PATENT OFFICE
CERTIFICATE OF CORRECTION

PATENT NO. : 4,332,809
DATED : Jun. 1, 1982
INVENTOR(S) : Honma et al.

It is certified that error appears in the above-identified patent and that said Letters Patent are hereby corrected as shown below:

column 9, line 48 correct "minutes"

column 12, line 68 correct "4-methyl-6-(4-N-methyl-N-benzyloxcarbonylamino-"

column 20, line 8 change "4-methyl-6-(4-methyl-N-ben-" to --4-methyl-6-(4-N-methyl-N-ben- -- column 21, line 58 change "mannse" to --manner--

Signed and Sealed this

Twelfth Day of April 1983

[SEAL]

Attest:

GERALD J. MOSSINGHOFF

Attesting Officer        Commissioner of Patents and Trademarks